United States Patent [19]

Mason et al.

[11] Patent Number: 4,963,674

[45] Date of Patent: Oct. 16, 1990

[54] PURIFICATION OF CYANURIC ACID

[75] Inventors: Robert W. Mason, Lake Charles; Thomas C. Parker, Sulphur, both of La.

[73] Assignee: Olin Corporation, Cheshire, Conn.

[21] Appl. No.: 454,653

[22] Filed: Dec. 21, 1989

Related U.S. Application Data

[63] Continuation-in-part of Ser. No. 164,671, Mar. 7, 1988, abandoned.

[51] Int. Cl.$^5$ .......................................... C07D 251/32
[52] U.S. Cl. .................................................... 544/192
[58] Field of Search ......................................... 544/192

[56] References Cited

U.S. PATENT DOCUMENTS

| | | | |
|---|---|---|---|
| 2,943,088 | 6/1960 | Westfall | 544/192 |
| 3,107,244 | 10/1963 | Robertson | 544/192 |
| 3,969,352 | 7/1976 | Berkowitz | 544/192 |
| 4,029,660 | 6/1977 | Berkowitz | 544/192 |

OTHER PUBLICATIONS

Japanese 76–059133 Derwent Abstract 11/26/77.

*Primary Examiner*—John M. Ford
*Attorney, Agent, or Firm*—James B. Haglind; Paul Weinstein

[57] ABSTRACT

A process for the purification of crude cyanuric acid containing aminotriazine compounds as impurities which comprises digesting the crude cyanuric acid in an aqueous solution containing low concentrations of a mineral acid. The mineral acid is, for example sulfuric acid, nitric acid, hydrochloric acid, or phosphoric acid. The digestion is operated at a temperature in the range of from about 120° C. and about 220° C. and autogenous pressure using a stoichiometric ratio of sulfuric acid to aminotriazine compounds of less than 1, to produce a slurry of purified cyanuric acid in an acid depleted ammonium sulfate solution.

Purification of cyanuric acid by the process of the present invention permits a substantial reduction in the amounts of acid used in the digestion and the base required for ammonia stripping and neutralization of the spent acid from the digestion. This provides significant cost savings in the digestion and waste treatment methods.

15 Claims, 1 Drawing Sheet

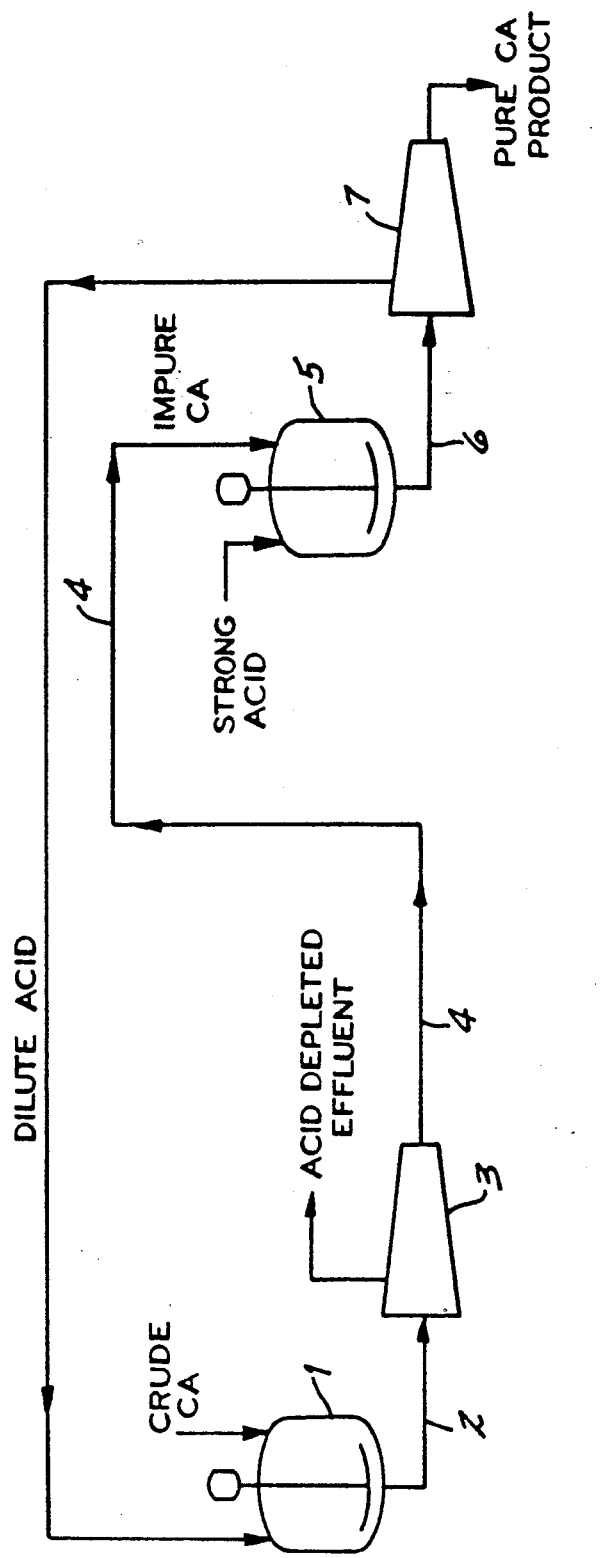

PURIFICATION OF CYANURIC ACID

This application is a continuation-in part of U.S. Ser. No. 07/164,671, filed Mar. 7, 1988, now abandoned.

This invention relates to the production of cyanuric acid. More particularly, this invention relates to the purification of crude cyanuric acid.

Cyanuric acid is a commercial product used in the production of chloroisocyanuric acid bleaching agents and as a stabilizer for available chlorine-containing compounds used in sanitizing swimming pools.

Cyanuric acid is made commercially by the pyrolysis of urea, biuret, or urea cyanurate or mixtures thereof. The product produced contains significant concentrations of amino-substituted triazine compounds such as ammelide and ammeline as by-products or impurities.

The crude cyanuric acid to be purified normally contains 70 to 80 percent by weight of cyanuric acid, 20 to 30 percent of aminotriazine compounds such as ammelide and ammeline as impurities, and minor amounts of other impurities such as urea.

In one method of removing these impurities, the crude cyanuric acid is digested or hydrolyzed in an aqueous mineral acid solution. Mineral acids which have been suggested for the digestion process include sulfuric, nitric, hydrochloric and phosphoric, with sulfuric acid being most frequently used.

The acid digestion treatment operates by dissolving all acid-soluble impurities present in the reaction mixture. It hydrolyzes aminotriazine impurities such as ammelide and ammeline to yield cyanuric acid and a corresponding ammonium salt. At the conclusion of the digestion period, purified cyanuric acid is present as a slurry in an acidic ammonium salt solution.

Acid digestion processes, while being commercially effective processes for purifying the cyanuric acid, have caused, in the past, numerous pollution problems with regard to the acid digestion effluent solutions. The acid digestion effluents have been partially or entirely discarded as an untreated waste because the treatment to make them safe for discharge is difficult and expensive. Untreated acid digestion solutions discharged into natural waterways, however, have disrupted and often destroyed natural fauna and flora. Presently, the acid digestion effluent solutions must be treated, for example, by neutralizing the acid with base, stripping off the ammonia, and then readjusting the pH with acid. The treatment costs for the acid digestion effluent solutions in a commercial process are very substantial.

Previous methods of cyanuric acid purification by acid digestion include U.S. Pat. No. 2,943,088, published Jun. 28, 1960 by R. H. Westfall, which teaches that crude cyanuric acid can be digested in aqueous acid solutions having acid concentrations of 1-25 percent at pressures of 0 to 100 p.s.i.g.

J. A. Robertson in U.S. Pat. No. 3,107,244, published Oct. 15, 1963 describes an acid digestion process which uses a strong mineral acid (2-5N) at the atmospheric boiling point of the acid solution.

Solutions of ammonium hydrogen salts at temperatures of 160° to 220° C. and autogeneous pressures i.e., 130-275 p.s.i.g. are used to digest crude cyanuric acid by S. Berkowitz in the processes described in U.S. Pat. Nos. 3,969,352, issued Jul. 13, 1976 and 4,029,660, issued Jun. 14, 1977.

In all of these processes the amount of acid used is in excess of that required to digest the aminotriazine impurities, such as ammelide or ammeline, in the crude cyanuric acid.

Japanese Patent No. 81-16149, issued Apr. 14, 1981 to Shikohu Chem. Ind. K. K. describes a process for treating waste sulfuric acid from the purification of cyanuric acid by reacting the acid with ammonia to produce concentrated ammonium sulfate solutions having higher than 30 percent by weight of $(NH_4)_2SO_4$. The solution is then neutralized to a pH above 3.5 to precipitate ammelide and then to a pH of 7-10 to precipitate cyanuric acid.

In this as well as the other processes described above, the neutralization of the acidic effluent requires large quantities of a base such as caustic soda and subsequently large expenses for treatment.

Now it has been found that the amount of acid used in crude cyanuric acid purification can be decreased and the waste treatment costs of the acidic effluent substantially reduced in a process for the purification of crude cyanuric acid containing aminotriazine compounds as impurities which comprises digesting the crude cyanuric acid in an aqueous solution containing low concentrations of a mineral acid at a temperature in the range of from about 120° C. and about 220° C. and autogenous pressure, wherein the stoichiometric ratio of mineral acid to aminotriazine compounds is less than 1, to produce a slurry of purified cyanuric acid in an acid depleted ammonium salt solution.

The FIGURE is a schematic flow sheet illustrating one embodiment of the process of the present invention.

Crude cyanuric acid to be purified by the removal of amino-substituted triazine compound is fed to pressurized reactor 1. Also charged to pressurized reactor 1 is a dilute acid solution for digestion of the crude cyanuric acid. A slurry of impure cyanuric acid in an acid depleted effluent is conveyed from pressurized reactor 1 through line 2 to separator 3. In separator 3 the impure cyanuric acid is separated from the acid depleted ammonium salt solution and charged to reactor 5 through line 4. Strong acid is charged to reactor 5 to digest the impure cyanuric acid, preferably at atmospheric pressure, to produce a slurry of pure cyanuric acid in a dilute acid. This slurry is fed through line 6 to separator 7 where the pure cyanuric acid is recovered as the product and a dilute acid solution is recycled to pressurized reactor 1.

In more detail, the novel process of the present invention purifies crude cyanuric acid containing as impurities aminotriazine compounds such as ammelide and ammeline. The crude cyanuric acid normally contains 20 to 30 percent by weight of the aminotriazine compound impurities where the cyanuric acid is produced by commercial processes which pyrolyze urea, biuret, urea cyanurate, or mixtures thereof.

To remove the aminotriazine compound impurities, the crude cyanuric acid is digested in an aqueous solution having low concentrations of mineral acid such as sulfuric acid, nitric acid, hydrochloric acid, or phosphoric acid. To simplify the disclosure, the process will be described using sulfuric acid as the mineral acid, which is the preferred embodiment.

In the digestion reaction, the purification of the cyanuric acid results from the hydrolysis of the aminotriazine compound impurities. The hydrolysis occurs by consuming one hydronium ion present in the aqueous acid solution for each amino group to be hydrolyzed and producing an ammonium ion as represented by the following:

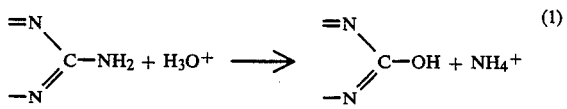

$$H_2SO_4 + H_2O \rightarrow H_3O^+ + HSO_4^- \qquad (2)$$

$$HSO_4^- + H_2O \rightleftharpoons H_3O^+ + SO_4^= \qquad (3)$$

Hydronium ions are present by the direct ionization of the sulfuric acid which, depending on the pH, also forms bisulfate and/or sulfate ions. The ionization is represented by the following:

The aqueous solutions of sulfuric acid employed in the digestion include those having low concentrations of $H_2SO_4$ which will substantially digest the aminotriazine compound impurities present. Suitable solutions are those having a mixture of bisulfate ions and sulfate ions and include, for example, those having concentrations in the range of from about 3 to about 10, preferably from about 3.5 to about 8, and more preferably from about 4 to about 6 percent by weight of $H_2SO_4$, although solutions having lower concentrations may be employed. The aqueous solution employed may, in addition to $H_2SO_4$, also contain salts such as ammonium bisulfate or ammonium sulfate and mixtures thereof, as well as other salts which will not react with or contaminate the cyanuric acid.

In the process of the present invention the stoichiometric ratio of $H_2SO_4$ used in the digestion of aminotriazine compound impurities is less than 1, for example, from about 0.5 to about 0.95, and preferably from about 0.6 to about 0.9.

The digestion is carried out at temperatures in the range of from about 120° to about 220° C., preferably from about 130° to about 190° C. and more preferably from about 140° to about 160° C. in a reactor at autogeneous pressures. At these reaction temperatures the pressures are moderate, for example, in the range from about 25 to about 150, preferably from about 25 to about 100, and more preferably from about 25 to about 75 p.s.i.g. Digestion under these conditions utilizes the hydronium ion produced from the conversion of bisulfate ion to sulfate ion for hydrolysis of the aminotriazine compound impurities. This reaction conversion, represented by equation (3), is ineffective at lower temperatures and lower pressures, i.e., atmospheric pressure reactions.

Any suitable reaction time may be used and the digestion reaction is continued until the ammonium sulfate solution formed is substantially deplete of acid. This acid depleted effluent can than be treated at substantially reduced costs and discharged. Acid depleted ammonium sulfate solutions included those having less than about 3 percent by weight of $H_2SO_4$, for example, from about 0 to about 3, and preferably from about 0 to about 2 percent by weight of $H_2SO_4$.

A slurry of purified cyanuric acid in an ammonium sulfate mother liquor is discharged from the digestion reactor, cooled, and separated from the mother liquor, for example, by filtration or centrifugation.

The mother liquor, an ammonium sulfate solution depleted of bisulfate ions and substantially depleted of hydronium ions, is treated to strip off the ammonia present, for example, by reaction with a base such as caustic soda. After neutralization, the mother liquor can be discharged directly to a watercourse.

In a preferred embodiment, the crude cyanuric acid is digested in two steps, the first of which is the novel process of the present invention. In the second step, the cyanuric acid from the first digestion step is treated in a second digestion step. In this step, the stoichiometric ratio of sulfuric acid to aminotriazine compounds is greater than 1 and the aqueous solution has a concentration of $H_2SO_4$ such that the bisulfate ion is predominant. While the second digestion step may be conducted at temperatures corresponding to those in the first digestion step, it is preferred to operate the second digestion step at lower temperatures and pressures, preferably at the boiling point of the aqueous acid solution at about atmospheric pressure.

In the second digestion step, any remaining aminotriazine compound impurities produce a very high purity cyanuric acid product.

Purification of cyanuric acid by the process of the present invention permits a substantial reduction in the amounts of acid used in the digestion and the base required for ammonia stripping and neutralization of the spent acid from the digestion. This provides significant cost savings in the digestion and waste treatment methods.

The invention is further illustrated by the following examples with no intention of being limited thereby. Unless otherwise stated, all parts and percentages are by weight.

EXAMPLE 1

To a pressure vessel equipped with an agitator and electric heating elements was charged 643.5 parts by weight of crude cyanuric acid containing 76.8 percent by weight of cyanuric acid, 18.5 percent by weight of ammelide and 4.6 percent by weight of ammeline. Also charged to the reactor was an aqueous solution of sulfuric acid having an initial sulfuric acid content of 1.98 percent, to form a reaction mixture with a stoichiometric ratio of $H_2SO_4$ to the combined amounts of ammelide and ammeline of 0.65. The pressure vessel was sealed, the slurry agitated and heated to 160° C. and the digestion conducted at an autogeneous pressure of about 95 p.s.i.g. Samples of the reaction mixture were withdrawn periodically to follow the reaction progress. After four hours the digestion was stopped and the slurry of purified cyanuric acid in an ammonium sulfate solution withdrawn from the reactor. The purified cyanuric acid product by analysis contained 98.61 percent by weight of cyanuric acid and 0.83 percent by weight of ammelide and 0.57 percent by weight of ammeline. The acid depleted ammonium sulfate ion contained 0.12 percent by weight of sulfuric acid.

EXAMPLE 2

A pressure vessel equipped with an agitator and electric heating elements was charged with a crude cyanuric acid (643.5 g) containing 76.8 percent by weight of cyanuric acid, 18.5 percent by weight of ammelide and 4.6 percent by weight of ammeline was charged. Also charged to the pressure vessel was 2250 g of an aqueous slurry of ammonium sulfate containing 6.7 percent by weight of sulfuric acid to form a reaction mixture having a stoichiometric ratio of $H_2SO_4$ to the combined amounts of ammelide and ammeline of 1.2. The pressure vessel was sealed, the slurry agitated and heated to 160° C. over a 1.5 hour period. During the heating the pressure increased to about 60 p.s.i.g. Samples of the reaction mixture were taken periodically and the concentration of the sulfuric acid in the reaction mixture was measured. The heating was continued for an additional 1.5 hours. The purified cyanuric acid slurry was filtered and the filtrate, containing 2.93 percent sulfuric acid, was admixed with 429 g water, 13 g of concentrated $H_2SO_4$, 143 g ammonium sulfate, and 643.5 g of crude cyanuric acid added. This slurry having a stoichiometric ratio of $H_2SO_4$ to the combined amounts of ammelide and ammeline impurities of 0.6 was recharged to the pressure vessel, heated to a temperature of 160° C., and the autogeneous pressure was 120 p.s.i.g. After a period of 3 hours, the acid concentration had dropped to 0 and the digestion was discontinued. The purity of the cyanuric acid, from both cycles, was greater than 99 percent.

EXAMPLE 3

To the apparatus employed in Example 1 was charged 643.5 parts by weight of crude cyanuric acid (82.18 percent by weight of cyanuric acid, 15.07 percent by weight of ammelide and 2.3 percent by weight of ammeline), 75.5 parts of 98% sulfuric acid, 1500 parts by water, and 1500 parts of ammonium sulfate were heated to 181°–189° C., (autogenous pressure 100–125 psig) for four hours. The recovered cyanuric acid product (533.1 parts, 83% overall yield) contained by weight 99.78 percent of cyanuric acid, 0.45 percent of urea, 0.09 percent of ammelide, and 0.07 percent of ammeline. The recovered filtrate had been depleted to 0.07% by weight of sulfuric acid.

What is claimed is:

1. A process for the purification of crude cyanuric acid containing aminotriazine compounds as impurities which comprises digesting the crude cyanuric acid in an aqueous solution containing low concentrations of a mineral acid selected from the group consisting of sulfuric acid, nitric acid, hydrochloric acid, and phosphoric acid, at a temperature in the range of from about 120° C. and about 220° C. and autogenous pressures, wherein the stoichiometric ratio of mineral acid to aminotriazine compounds is less than 1, to produce a slurry of purified cyanuric acid in an acid depleted ammonium salt solution.

2. The process of claim 1 in which the mineral acid in the aqueous solution is sulfuric acid.

3. The process of claim 2 in which the acid depleted ammonium sulfate solution has a concentration of $H_2SO_4$ in the range of from about 0 to about 3 percent by weight.

4. The process of claim 2 in which the stoichiometric ratio of sulfuric acid to aminotriazine compounds is from about 0.5 to about 0.95.

5. The process of claim 2 in which the aqueous solution is selected from the group consisting of sulfuric acid, ammonium sulfate, ammonium bisulfate, and mixtures thereof.

6. The process of claim 2 in which the autogenous pressure is in the range of from about 25 to about 150 p.s.i.g.

7. The process of claim 3 in which the temperature of the digestion reaction is from about 130° to about 190° C.

8. The process of claim 7 in which the aqueous solution has a concentration of from about 3 to about 8 percent by weight of $H_2SO_4$.

9. The process of claim 8 in which the stoichiometric ratio of sulfuric acid to aminotriazine compounds is from about 0.6 to about 0.9.

10. The process of claim 9 in which the acid depleted ammonium sulfate solution has a concentration of $H_2SO_4$ in the range of from about 0 to about 3 by weight.

11. A process for the purification of crude cyanuric acid containing aminotriazine compounds as impurities which comprises:
    (a) digesting the crude cyanuric acid in a first aqueous solution containing low concentrations of sulfuric acid, wherein the stoichiometric ratio of sulfuric acid to aminotriazine compounds is less than 1, and at a temperature in the range of from about 120° C. to about 220° C. and autogenous pressure, to produce a slurry of cyanuric acid in an acid depleted ammonium sulfate solution, wherein the cyanuric acid contains a reduced concentration of aminotriazine compounds,
    (b) separating the cyanuric acid from the acid depleted ammonium sulfate solution, and
    (c) digesting the cyanuric acid in a second aqueous solution containing sulfuric acid, wherein the stoichiometric ratio of sulfuric acid to aminotriazine compounds is greater than 1, to produce a purified cyanuric acid in an ammonium bisulfate solution.

12. The process of claim 11 in which the first aqueous solution contains from about 3 to about 10 percent by weight of $H_2SO_4$.

13. The process of claim 11 in which said acid depleted ammonium sulfate solution contains from about 0 to about 3 percent by weight of $H_2SO_4$.

14. The process of claim 11 in which the digestion in the second aqueous solution is carried out at a lower temperature and a lower pressure than the digestion in the first aqueous solution.

15. The process of claim 11 in which the purified cyanuric acid is separated from the ammonium bisulfate solution and the ammonium bisulfate solution is recycled to step (a).

* * * * *